United States Patent
Vandeputte

(10) Patent No.: US 8,425,942 B2
(45) Date of Patent: Apr. 23, 2013

(54) METHOD FOR STERILIZING UNHEATED RAW HONEY, A HONEY-BASED WOUND CARE PREPARATION, A WOUND CARE TREATMENT PRODUCT, AND A BISCUIT BASED ON HONEY

(75) Inventor: Jan Vandeputte, Varsenare (BE)

(73) Assignee: CNCI BVBA, Varsenare (BE)

( * ) Notice: Subject to any disclaimer, the term of this patent is extended or adjusted under 35 U.S.C. 154(b) by 595 days.

(21) Appl. No.: 12/311,753

(22) PCT Filed: Oct. 23, 2007

(86) PCT No.: PCT/EP2007/009182
§ 371 (c)(1),
(2), (4) Date: Apr. 10, 2009

(87) PCT Pub. No.: WO2008/049578
PCT Pub. Date: May 2, 2008

(65) Prior Publication Data
US 2010/0028408 A1    Feb. 4, 2010

(30) Foreign Application Priority Data
Oct. 27, 2006   (BE) .................................. 2006/0525

(51) Int. Cl.
*A61K 35/64*    (2006.01)
*A61L 2/00*    (2006.01)
*A61L 2/20*    (2006.01)
*A61L 101/10*    (2006.01)

(52) U.S. Cl.
USPC ........ 424/537; 424/539; 422/28; 422/186.08; 422/186.07

(58) Field of Classification Search .................. 424/443, 424/537, 484; 426/103, 93; 422/28
See application file for complete search history.

(56) References Cited

U.S. PATENT DOCUMENTS
6,294,211 B1 * 9/2001 Yuan et al. ..................... 426/235
6,780,331 B2 * 8/2004 Galatro et al. ............. 210/747.8
2009/0291122 A1 * 11/2009 Vandeputte ................... 424/443

FOREIGN PATENT DOCUMENTS
WO       WO 01/47373 A1    5/2001

OTHER PUBLICATIONS

Gunther B. Paulin, The Divine Prescription and Science of Health and Healing (1995) p. 446 [Downloaded May 8, 2011] [Retrieved from Google Books, internet <URL: http://books.google.com/books?id=nNdmNbCcWoEC&pg=PA446&dq=healing+hand+-+honey&hl=en&ei=jmDHTZGEMM_SgQervqDLBA&sa=X&oi=book_result&ct=book-thumbnail&resnum=6&ved=0CHgQ6wEwBQ#v=onepage&q=healing%20hand%20-%20honey&f=false >](2 pages).*

(Continued)

*Primary Examiner* — Jason M Sims
*Assistant Examiner* — Miriam A Levin
(74) *Attorney, Agent, or Firm* — James Creighton Wray

(57) ABSTRACT

The invention relates to a method for sterilizing raw, unheated honey, wherein the raw, unheated honey is sterilized by ozonizing it by using an ozone generator. The invention also relates to a honey-based wound care preparation, wherein said preparation comprises raw, unheated ozonized honey that has been ozonized by a method according to the invention. The invention also relates to a wound care treatment product comprising a honey-based preparation, wherein the said wound care treatment product comprises a preparation according to the invention. Finally, the invention relates to a biscuit based on honey and food fibers and/or by-products of food fibers, wherein the biscuit is prepared from ozonized food fibers and/or by-products of food fibers and raw, unheated ozonized honey that has been ozonized by a method according to the invention.

5 Claims, 1 Drawing Sheet

OTHER PUBLICATIONS

Figure 1:
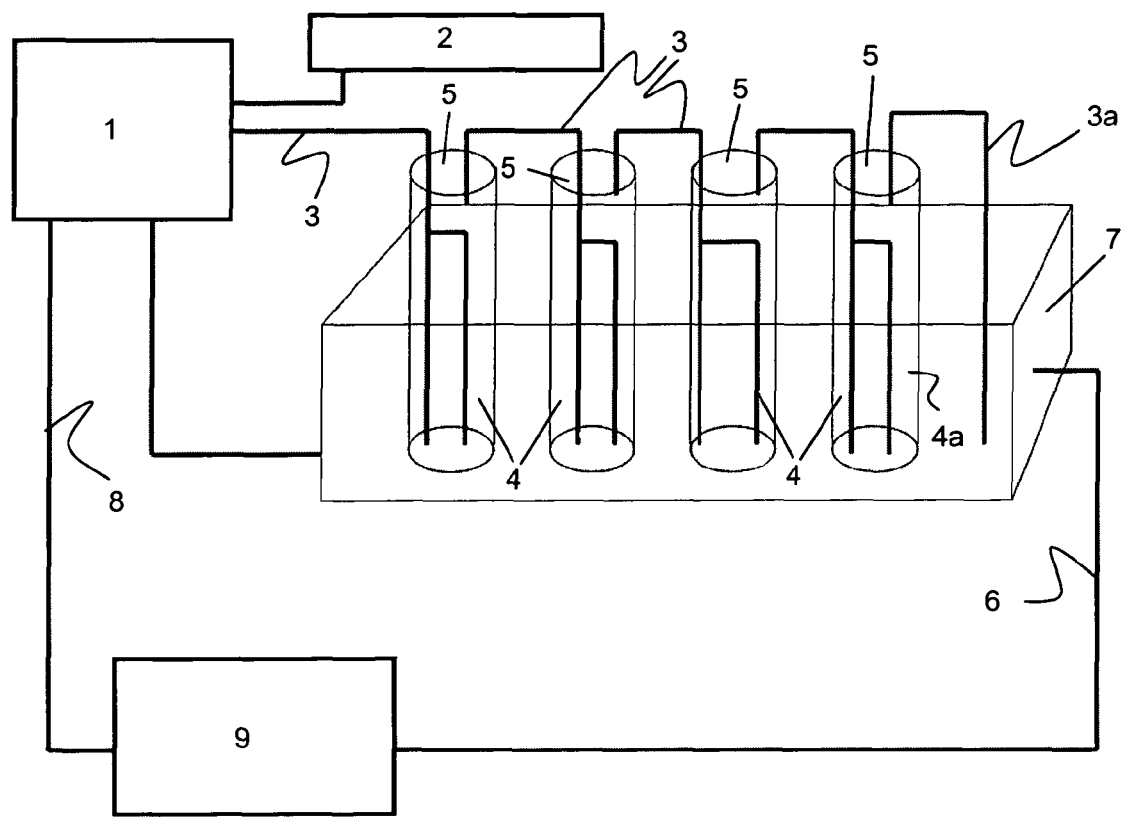

CN 1216229 A (hereinafter "CN 229") (Derwent Abstract 1999-430987 (1999), [Retrieved from EAST]), 1 page.*
CN 1887108 A (hereinafter "CN 108") (Derwent Abstract 2007-344918 (Jan. 3, 2007) [Retrieved from EAST}0, 1 page.*
Chen et al., CN 1216229 A (May 1999), Dialogue Machine Translation [Downloaded Apr. 27, 2012] [Retrieved using USPTO STIC translation services from internet <URL: http://toolkit.dialogue.com/intranet/cgi/present >], 5 pages.*
Haiping, CN 1887108 (Jan. 2007),Dialogue Machine Translation [Downloaded Apr. 27, 2012] [Retrieved using USPTO STIC translation services from internet <URL: http://toolkit.dialogue.com/intranet/cgi/present >], 8 pages.*
Gu (CN 1 887 108, manual translation by Irina Knizhnik (Aug. 15, 2012)), 4 pages.*
Zhou et al. (CN 2 16 229, manual translation by Irina Knizhnik (Aug. 9, 2012)), 2 pages.*
CN 216229 (May 12, 1999)—manual translation by USPTO translator Irina Knizhnik (Aug. 9, 2012) (3 pages).*
CN 1887108 (Jan. 3, 2007)—manual translation by UPSTO translator Irina Knizhnik (Aug. 15, 2012) (4 pages).*
Molan, P.C. et al.;"The Effect of Gamma-irradiation on the Antibacterial Activity of Honey"; Journal of Pharmacy and Pharmacology, vol. 48, No. 11, Nov. 1996; pp. 1206-1209; (XP000994783).
Postmes, T. et al.; "The sterilization of honey with cobalt 60 gamma radiation: a study of honey spiked with spores of *Clostridium botulinum* and *Bacillus subtilis*"; Experientia, vol. 51,No. 9-10; pp. 986-989; (XP002169769).
Molan, P.C.; "Honey as a topical antibacterial agent for treatment of infected wounds"; Retrieved from internet url: http://www.worldwidewounds.com/2001/november/Molan/honey-as-topical-agent.html (XP002435487).

* cited by examiner

METHOD FOR STERILIZING UNHEATED RAW HONEY, A HONEY-BASED WOUND CARE PREPARATION, A WOUND CARE TREATMENT PRODUCT, AND A BISCUIT BASED ON HONEY

This application claims the benefit of Belgian Application No. 2006/0525 filed Oct. 27, 2006 and PCT/EP2007/009182 filed Oct. 23, 2007, which are hereby incorporated by reference in their entirety.

The present invention relates to a method for sterilizing unheated raw honey, a honey-based wound care preparation, and a wound care treatment product. It also relates to a biscuit made of food fibres and/or by-products of food fibres and honey, the said biscuit being unbaked.

The use of honey for treating acute or chronic wounds has a history going back many centuries (to about 2000 before Christ), but it has been scientifically recognized only quite recently. The use of alternative therapies for the treatment of infected wounds is nowadays of enlarged interest, owing to the widespread development of antibiotic-resistant bacteria. Numerous investigations have so far been carried out to study the effects of honey.

The oldest written instruction for the medicinal use of honey is found in a Samaritan clay tablet (ca. 2000 before Christ), described in Kramer, S. N., Levey, *An older pharmacopoeia*, Journal of the American Medical Association (1954), 155 (1), p. 26. In Asia, honey has always been a main ingredient of medicines. It can be found in the Chinese literature dating back to 2000 before Christ. Many recipes can also be found in the VEDA, the holy book of the peoples who lived in the area of the Ganges valley around 1000 before Christ [see Mullick, N. P., *Honey and beekeeping in the Scriptures and after*, Indian Bee Journal (1944) (5/6), pp. 108-114].

Honey had numerous medical uses in ancient Egypt. Several papyrus scrolls have been found and translated. The Ebers papyrus scroll (from about 1550 before Christ) comprises 147 recipes for external applications of honey. The Smith papyrus scroll shows an interesting picture of medical and surgical applications 4000 years ago. Even 48 case studies are described there [see Manjo, G., *The Healing Hand* (1975), Harvard University Press, Cambridge, Mass., USA, p. 571].

The use of honey is also mentioned in a few verses of the Bible. In about 1700 before Christ, Jacob told his sons to take some balsam and some honey as a gift for their brother Joseph (*Genesis*, 43.11). The Koran says that God inspired the bees to eat from all fruits so that they can make a liquid with different colours and a healing effect for man [see Manjo, G., *The Healing Hand* (1975), Harvard University Press, Cambridge, Mass., USA, p. 571].

In this way, the recipes were transmitted from Egypt to ancient Greece, and although Hippocrates, the father of modern medicine, did not talk about these recipes, he praised the possibilities of honey in the following pronouncement "... it cleans sores and ulcers, softens the hard crust on the lips, heals carbuncles and suppurating wounds".

Eventually, many recipes are known, but then the dark ages descended, and little can be found about the use of honey then. From 1446 onwards, some writings appeared again wherein the use of honey for wounds was described.

Finally, honey was never denounced, but it remained in the realm of alternative medicine or was regarded as a granny's remedy.

It was not until 1759 that an English physician wrote a complete book about honey, wherein he tried to convince his colleagues to take honey seriously as a medicine for certain diseases and problems [see Hill, J., *The Virtues of Honey* (1957), Davis, London, UK].

However, another 230 years had to elapse before a doctor again drew attention to honey as a medicine in 1989, i.e. Molan, P.& Brett, M., *Honey has potential as a dressing for wounds infected with MRSA* (1989), The Second Australian Wound Management Association Conference, held in Brisbane, Australia on 18-21 Mar. 1998]. According to Molan, P. C., The role of honey in wound care, *Journal of Wound Care*, vol. 8(8), pp. 145-149, honey has 5 important properties, i.e.

1. The antibacterial activity [see Molan, P. C., (1992) *The antibacterial activity of honey*, 1. *The nature of the antibacterial activity*, Bee World, 73(1), pp. 5-28, and Molan, P. C., (1992) *The antibacterial activity of honey*, 2. *Variation in potency of the antibacterial activity*, Bee World, 73(2), pp. 59-72]. This activity is based on two mechanisms, on the one hand the hyperosmolarity of honey and on the other hand the intrinsic antibacterial activity of the honey. The hyperosmolarity of the honey ensures that honey draws water out of tissues. This produces a low water vapour pressure or $a_w$ value (the amount of water a bacterium needs for survival). Honey has an extremely low $a_w$ value (0.45-0.70). Comparison of this value with the $a_w$ values of bacteria and fungi shows that the $a_w$ value of honey is well below that of bacteria and fungi, so that honey inhibits the growth of these bacteria and fungi. (The growth of *Staphylococcus aureus* is fully inhibited when the $a_w$ value is below 0.86) [see Cooper, R. A., Molan, P. C. & Harding, K. G., *Antibacterial activity of honey against strains of Staphylococcus aureus, isolated from infected wounds*, Journal of the Royal Society of Medicine (1999), 92, pp. 283-285]. The intrinsic antibacterial activity is actually the most important in this antibacterial property. Because of this activity, honey gives more advantages and a greater efficacy than the use of sugar. The intrinsic antibacterial activity is based on the effect of the enzyme glucose oxidase, which comes from the bee's food juice gland. In a dilute solution, this enzyme converts glucose into gluconic acid and hydrogen peroxide, the latter being an efficient antimicrobial agent. Active diluted honey provides in a slow release of hydrogen peroxide such that this substance serves as an effective antiseptic. The concentration of hydrogen peroxide built up in an hour is about one-thousandth of that present in a 3% solution of hydrogen peroxide, which causes cellular damage. However, out of the literature it seems that the concentration built up is sufficient to kill bacteria, as demonstrated by animal experiments.

2. The deodorant activity. The removal of bad odour is a logical consequence of the antibacterial action of honey. Bad odour is caused by the waste materials produced by bacteria. If the number of bacteria decreases, the number of waste products also decreases. The speed of the deodorant action probably depends on the disappearance of bacteria. This deodorant action is greatly appreciated by patients with oncological wounds.

3. The debriding activity. The debriding activity of honey has only been recognized in the last few decades. The debriding effect is caused by the stimulation of the autolysis of the necrotic tissue. This happens by means of the stimulation of bodily enzymes by the honey and by means of the hyperosmolarity of honey through which the necrosis undergoes a tissue change [see Subrahmanyam, M., *A prospective randomised clinical and*

*histological study of superficial burn wound healing with honey and silver sulphadiazine*, Burns (1998), 24 (2), pp. 157-161].

4. The anti-inflammatory activity. The anti-inflammatory activity of honey has been demonstrated by histological studies on experimental wounds with animals. Even when there is no infection, the anti-inflammatory activity remains present. It is probably due to the reduction of the number of inflammatory cells penetrating the wound. Clinical observations confirm a reduction of infection, reduced oedema, decreasing exudation and a soothing effect on the pain when honey is applied to the wound [see Efem, S. E. E., *Clinical observations on the wound healing properties of honey* (1988), Br. J. Surg., 75, pp. 679-681].

5. The stimulation of tissue growth. Honey stimulates the formation of clean and healthy granulation tissues and stimulates epithelialization as demonstrated histologically in animal experiments. This may be the consequence of the release of hydrogen peroxide, which stimulates in low concentration the angiogenesis and the growth of fibroblasts. Enlarged angiogenesis produces more oxygen, which for tissue regeneration is a stimulating factor. A second cause may lie in the acidification of the wound. Honey has a pH of 3 to 4. In the case of external acidification, it has been shown that healing is stimulated because more oxygen is released by the haemoglobin. As third theory, it is thought that the nutritive content of honey would stimulate the growth. The honey after all comprises a large set of amino acids, vitamins, trace elements and a large amount of easily absorbable sugars. Further research will have to point out which of these three hypotheses is correct, or whether there is a combination of them. In any case, this faster epithelialization leads to increased debridement, less granulation tissue and less scar tissue.

In the early history, honey was used in the pure state. Throughout the centuries, various products were added to the honey. The Egyptians diluted the honey with fat and in the Middle Ages both fat and egg-white were added. In the 20th century, several scientists investigated the action of pure honey. Out of these investigations, former mentioned properties could be deducted. This pure honey is however not patient-friendly. Because of the strong osmotic pressure, the honey causes a too severe pain to the patients. A honey ointment that possesses all the characteristics of honey but that is more patient-friendly has consequently to be looked for.

In the last 5 years, a number of honey-based wound care preparations have been launched on the market, and several patents can be found thereof, such as for example U.S. Pat. No. 6,174,535, U.S. Pat. No. 5,980,875, WO 02130467 and WO 2004/000339.

These patent applications concentrate on the way honey should be defined, such as in terms of the amount of hydrogen peroxide produced by the honey and in terms of other parameters. Also in NL 1 016 398, it is specifically mentioned that honey must be irradiated for treating wounds. Honey after all comprises a set of bacteria, fungi and yeasts. Some of these bacteria are anaerobic, such as the *Clostridium botulinum* strains. These are generally found in raw, unheated and untreated honey and can cause gas gangrene when these are applied to a wound. In this way, 270 samples of a non-treated honey out of seven different countries were found to be contaminated with 40-80 spores per gram of honey [see Postmes, T., van den Bogaard, A. E. and Hazen, M., *The sterilization of honey with cobalt 60 gamma radiation: a study of honey spiked with spores of Clostridium botulinum and Bacillus subtilis*, Experientia 51 (1995), pp. 986-989]. Therefore, honey that is used for the preparation of a wound care gel or ointment is irradiated with an average dose of 10-30 kGy. The irradiation of honey with such high doses has only been used in the past five years, and when one determines the enzymatic activity (glucose oxidase) before and after the irradiation, than it is clear that most honey varieties all active enzymes that are produced by the honey no longer produce hydrogen peroxide. Some honey varieties are a little more resistant to radiation (this is generally accompanied by high flavenoids content), but these honey varieties produce so much gas during irradiation that the containers burst or overflow. During irradiation, the honey turns into a white cream with a lot of foam, and it takes a few weeks before the honey more or less regains its normal colour and consistency. It is also our experience (by conducting accelerated ageing tests with irradiated honey and honey-based wound care products) that this irradiated honey continues to form and produce gas for several years. This creates problems for the storage life of wound care products made with this irradiated honey. Furthermore, the gas produced acts as a kind of propellent that, when the tube is opened, pushes the ointment/gel rapidly out of the tube, wherein in a number of cases the tube completely empties. It is also our experience that ointments/gels that are made with (on the basis of) irradiated honey seem to turn brown quickly, i.e. within a year (in closed aluminium tubes), indicating that a caramelization process is induced by the irradiation of honey. This process of caramelization can be easily speeded up by exposing the ointment/gel to higher temperatures. When tubes with honey ointment are exposed to temperatures of over 28-35° C. for a period of two months, the ointment changes completely from a yellowish white cream to a dark brown sticky and crusty syrup. Some of the tubes even exploded during the test (within 2 months). From this it can be concluded that the standard irradiation of honey for use in wound care in fact destroys the honey through which its function/activity ends up.

The aim of the invention is on the one hand to provide a method for sterilizing unheated, raw honey and on the other hand to provide a honey-based wound care preparation, and a wound care treatment product comprising a honey-based preparation, wherein the raw, unheated honey retains all its original properties, and consequently does not damages the raw, unheated honey, but wherein the honey is substantially free of fungi and yeasts, and can be made sufficiently germ-free or sterile.

On the one hand, this aim of the invention is achieved by providing a method for sterilizing raw, unheated honey, wherein the raw, unheated honey is sterilized by means of ozonizing the honey using an ozone generator.

In a preferred embodiment of a method according to the invention, depending on the type of ozone generator, honey is ozonized in order to obtain a honey that comprises substantially no fungi and yeasts and with a maximum of 100 colony-forming units per gram of viable aerobic bacteria.

In a specially preferred embodiment of a method according to the invention, the honey is ozonized with an ozone generator that produces 120 g/hour (24 g/Nm$^3$) of ozone at a flow rate of 15 l/minute and an O$_2$ pressure of 1.2 bar.

In an advantageous embodiment of a method according to the invention, depending on the type of honey, the raw, unheated honey is heated to a temperature of at most 40° C. in order to make it sufficiently liquid, such that the ozone gas can come into optimal contact with the honey.

On the other hand, the aim of the invention is achieved by providing a preparation for wound care based on honey, wherein the preparation comprises raw, unheated honey that has been ozonized by the method according to the invention as described above.

In a preferred preparation according to the invention, the preparation comprises between 25 and 80 wt. % of ozonized honey with respect to the total composition of the preparation.

A preferred preparation according to the invention comprises one or more of the following ingredients selected from a PEG product, vegetable oil, glycerol, CMC (sodium carboxymethylcellulose), propylene glycol, aloe vera, lanolin, cod liver oil, oil of *Calendula officinalis*, sunflower-seed oil, grape-seed oil, soya-bean oil, avocado oil, glucose oxidase, superoxide dismutase (SOD), lactoperoxidase (LP), methylsulphonylmethane (MSM), lactoferrin (LF) and zinc oxide powder.

In a preferred embodiment of a preparation according to the invention, the preparation comprises one or more polymers chosen from a group consisting of vinyl polymers, polysaccharide polymers, glycosaminoglycan polymers, protein polymers, polyoxyethylene-polyoxypropylene polymers and acrylamide polymers.

In a preferred embodiment of a preparation according to the invention, the concentration of the polymers is between 0.5 and 30 wt. % of the total composition of the preparation, and the average molecular weight of the polymers is between 500 and 13,000,000.

In a favourable embodiment of a preparation according to the invention, the preparation comprises a lactoferrin concentration of between 0.0001 and 3.0 wt. %, with respect to the total composition of the preparation.

Finally, the aim of the invention is achieved by providing a wound care treatment product comprising a honey-based preparation, wherein the wound care treatment product comprises a preparation according to the invention as described above.

In a preferred embodiment of a wound care treatment product according to the invention, the wound care treatment product is a gel, an ointment, a cream, a tulle (fatty gauze), an impregnated polyurethane foam sheet or a hydrogel plate.

Furthermore, the use of honey in biscuits is also known, as for instance described in GB 821 883. In this patent application, it is described that, in order to preserve the characteristics of the honey as much as possible, the dried cereal mash is mixed with a diastase solution to form a thick paste at a temperature of about 42° C. In the there from resulting mass, it is possible to mix honey that was already warmed up, whereafter the whole is dried by means of spray drying or vacuum drying at a temperature of below 60° C.

The disadvantage of this biscuit however is that there still occurs a warming up of the honey through which not all its original characteristics are maintained.

Also a number of experiments have been carried out in the past with a combination of honey and cereal grains in order to make a biscuit for therapeutic use. For example, in WO 01/47, 373 it is described how a biscuit is made out of a combination of honey and cereal grains for alleviating gastric and intestinal complaints. In this patent application, it is described that the end product must not be heated or baked. By not heating the honey, the full properties of the ingredients are maintained, but this end product has a very limited shelf life because fungi and insect eggs make it inedible in less than three months.

It is therefore a further aim of the invention to provide a biscuit prepared from food fibres and/or by-products of food fibres and honey, wherein the biscuit is unbaked in order to retain the properties of raw, unheated honey, but wherein the biscuit is made easier to conserve.

This aim of the invention is achieved by providing a biscuit prepared from food fibres and/or by-products of food fibres and honey, wherein the biscuit is unbaked and wherein the biscuit is prepared from ozonized food fibres and/or by-products of food fibres and raw, unheated ozonized honey that has been ozonized by a method according to the invention as described above.

By making an unbaked biscuit out of ozonized food fibres and/or by-products of food fibres and ozonized honey, a biscuit with a better shelf-life can be made.

In a preferred embodiment of a biscuit according to the invention, the ozonized food fibres and/or ozonized by-products of food fibres are obtained by ozonization carried out in two stages.

More preferably these two stages exist of a first stage wherein ozone gas is passed into the food fibres for 1 to 2 hours and after a rest period of almost 12 hours, a second stage wherein for 5 to 8 hours ozone gas is blown through the food fibres. In this way, substantially all insect eggs are destroyed.

The food fibres preferably consist of cereal grains.

In an advantageous embodiment of a biscuit according to the invention, the biscuit can comprise one or more auxiliary substances such as glycerol and aromatic flavouring agents.

For example vanilla and/or an apple concentrate can be used as the aromatic flavouring agent.

In order to explain the characteristics of the present invention in more detail and to describe its other advantages and features, the following more detailed description deals with a method for sterilizing honey according to the invention, as well as with a wound care preparation and a wound care treatment product according to the invention.

In this detailed description, reference numbers are used to indicate the items in the attached FIG. 1, which illustrates an example of the scheme used for ozonizing honey. It will be obvious, however, that nothing in the following description can be regarded as a limitation of the scope of protection set out in the claims for the method, the wound care preparation and the wound care treatment product according to the invention.

The invention is also elucidated by some examples, which similarly cannot be seen as a limitation of the scope of protection of the invention per se, as described in the claims that follow.

In the method according to the invention, raw, unheated honey (not heated above 40° C.) and untreated honey is sterilized by ozonization, using an ozone generator. It should be mentioned that the definition of "raw, unheated honey" also covers honey that has been extracted in the cold state, because this does not change the composition of honey at all. A minimum irradiation of honey with up to 5 kGy is also permissible, provided that it does not alter the enzymatic activity of honey substantially.

Ozone ($O_3$) is the triatomic form of oxygen ($O_2$) and, being a very reactive gas, it is difficult to stabilize in a usable form for a long time. It is used as an antibacterial agent in various industrial processes, generally to sterilize water or surfaces where food products, such as for example raw meat, are prepared. This is usually done by bubbling the ozone gas generated through the medium. Ozone is a strong oxidant and can kill or destroy a large variety of viruses (including HIV), bacteria, fungi, yeasts and other toxins (it can kill *E. coli* 3125 times faster than chlorine, and it turns into ordinary oxygen during the disinfection process, without leaving behind harmful residues). Phenol compounds, pesticides, detergents, chemical wastes, and smelling substances (such as substances with a bad smell that are often formed in cancer wounds) are also oxidized by ozone faster than by chlorine, and without the formation of dangerous residues (see Chemical Technology—an Encyclopaedic Treatment, vol. 1, Barnes & Noble Inc., New York, pp. 82-83). For these reasons, ozone is the agent of first choice for disinfecting and purifying drinking water in a quite large field of applications. The Encyclopedia of Chemical Technology mentions on page 704 that ozone has an "all-or-none" effect as regards the destruction of bacteria. This effect is due to the high oxidation potential of ozone. Ozone is such a strong microbicide that only a few micrograms of it are needed in a litre for it to exert its microbicidal effect.

By bubbling ozone gas through liquefied honey in an ozone-resistant container (such as a stainless steel container), the fungi and yeasts are substantially completely destroyed, and the honey obtained is sufficiently free of bacteria. As regards the term "sufficiently free of bacteria" (also called "sterile"), Section 2.6.12 of the European Pharmacopoeia states that a wound care product such as an ointment or gel must not comprise more than 100 microorganisms (colony-forming units per gram), and it must be free of pathogens such as Staphylococcus aureus, Pseudomonas aeruginosa, etc. These last mentioned (the pathogenic bacteria) can generally not be found in honey.

As shown in FIG. 1, the following diagram can be used for ozonizing honey. For the production of the ozone, an ozone generator (1) is provided, that preferably produces 120 g/hour (24 g/Nm$^3$) ozone at a flow rate of 15 litres per minute with an $O_2$ pressure of 1.2 bar. The ozone generator (1) is cooled with cooling water coming from a cooler (9), wherein between the ozone generator (1) and the cooler (9) a cooling water pipe (8) is provided. The cooler (9) has an air-cooled cooling circuit and as a cooling agent preferably R407C is used. The water is cooled by means of the cooler (9) to a temperature of between 7 and 10° C. with a temperature of the surroundings of 35° C. The ozone is produced in the ozone generator (1) from oxygen that by means of an oxygen generator (2) is obtained from the air, this with an amount of 15 litres per minute and with a purity of 90% with a limit of +3% and 5% and at a pressure of 1 bar. The ozone produced is preferably conveyed by means of teflon pipes (3) to containers (4) wherein the honey to be ozonized is accommodated. These containers (4) are preferably made of stainless steel and preferably have a diameter of 30 cm and a height of 80 cm, and are furthermore provided with a hermetically coverable lid (5) having an on-off connection for the teflon pipes (3). The containers (4) are equipped with a discharge tap (not shown in the drawings) at the bottom for the removal of the ozonized honey. The teflon pipes (3) are preferably attached to each container (4) in a dedoubled way, and preferably reach down to the bottom of the containers (4). Furthermore, each container (4) is also provided with an ozone outlet (3a). The containers (4) are arranged in a stainless steel tank (7) wherein water is introduced that, depending on the type of honey, is warmed to a maximum temperature of 40° C. The water in the tank (7) comes from the ozone generator (1). The water in the stainless steel tank (7) can be additionally warmed further. The ozone flowing from the last container (4a) along the ozone outlet (3a) serves as decontaminator of the cooling water that is present in the stainless steel tank (7). Between the tank (7) and the cooler (9) there is also a water pipe (6) provided for conveying the water back from the tank (7) to the cooler (9). However, other arrangements giving to the same result are also possible.

The following four types of honey were tested in a simple experiment for the presence of microorganisms (including fungi and yeasts): Yucatan honey from Mexico, bio-honey from India, polyflora honey from Bulgaria and polyflora honey from Uruguay. For this purpose, 200 grams of each type of honey were ozonized for 30 minutes using an ozone generator producing 120 g/hour (24 g/Nm$^3$) ozone at a flow rate of 15 litres/minute with an $O_2$ pressure of 1.2 bar (as described above). In table 1, the results of the microbiological tests before and after the treatment of raw, unheated honey with ozone are shown. These tests were carried out in the laboratory of Chemiphar Nev. in the way specified for microbiological tests in Section 2.6.12 of the European Pharmacopoeia, this laboratory being accredited by Beltest in accordance with European Standard 45.001 (Certificate 031-T).

The results of these tests are shown in the tables 1 and 2.

TABLE 1

Microbiological results for various types of honey before the ozone treatment

| Type of honey | Before the ozone treatment | | | | |
|---|---|---|---|---|---|
| | Total viable micro-organisms | Yeasts + fungi | Total viable aerobes | Fungi | Yeasts |
| Yucatan honey from Mexico | 1000 | 40 | 960 | 40 | <10 |
| Bio-honey from India | 150 | <10 | 150 | <10 | <10 |
| Polyflora honey from Bulgaria | 250 | 20 | 230 | 20 | <10 |
| Polyflora honey from Uruguay | 260 | <10 | 260 | <10 | <10 |

TABLE 2

Microbiological results for various types of honey after ozone treatment for 30 minutes

| Type of honey | After ozone treatment for 30 minutes | | | | |
|---|---|---|---|---|---|
| | Total viable micro-organisms | Yeasts + fungi | Total viable aerobes | Fungi | Yeasts |
| Yucatan honey from Mexico | 40 | <10 | 40 | <10 | <10 |
| Bio-honey from India | 20 | <10 | 20 | <10 | <10 |
| Polyflora honey from Bulgaria | 20 | <10 | 20 | <10 | <10 |
| Polyflora honey from Uruguay | 25 | <10 | 25 | <10 | <10 |

As can be deducted from table 1, raw, unheated biological honey contains on average between 250 and 1000 colony-forming units per gram of microorganisms (total count, aerobic/anaerobic bacteria, fungi and yeasts). As can be seen from table 2, the ozone treatment of this honey for 30 minutes under the conditions described above reduces the number of microorganisms to 100 colony-forming units per gram or less. In the examples illustrated here, the number of microorganisms was reduced to 40 colony-forming units per gram or less. Consequently, by means of the ozone, also anaerobic bacteria, just like the spores, are killed (again to maximal 100 colony-forming units per gram).

A preparation for wound care on the basis of honey according to the invention comprises raw, unheated honey that has been ozonized by means of a method as described above. The preparation preferably comprises 25 to 80 wt. % of ozonized honey, with respect to the total composition of the preparation.

The preparation can comprise one or more of the following substances selected from a PEG product (Macrogol flakes), vegetable oil, glycerol, propylene glycol, aloe vera, sunflower-seed oil, grape-seed oil, soya-bean oil, avocado oil, lanolin, cod liver oil, marigold (calendula) oil, glucose oxidase, superoxide dismutase (SOD), lactoperoxidase (LP), methylsulphonylmethane (MSM), lactoferrin (LF) and zinc oxide powder.

The preparation can also comprise one or more polymers chosen from a group consisting of vinyl polymers (e.g. polyacrylic acid, polymethacrylic acid, polyvinylpyrrolidone and polyvinyl alcohol), polysaccharide polymers (e.g. cellulose, cellulose derivatives, glycosaminoglycans, agar, pectin, alginic acid, dextran, starch and chitosan), glycosaminoglycan polymers (e.g. hyaluronic acid, chondroitin, chondroitin-4-sulphate, chondroitin-6-sulphate, dermatan sulphate, keratan sulphate, heparin sulphate and heparin), protein polymers (e.g. collagen, gelatin and fibronectin), polyoxyethylene-polyoxypropylene polymers (e.g. a polyoxyethylene-polyoxypropylene block copolymer) and acrylamide polymers (e.g. polyacrylamide or polymethacrylamide). The polyoxyethylene-polyoxypropylene block copolymer F88 or F127 is preferred.

The polymer concentration is preferably from about 0.5 wt./wt. % to about 30 wt./wt. %, with respect to the total composition of the preparation, and the average molecular weight of the polymer is from about 500 to about 13,000,000.

The preparation can also comprise lactoferrin in an amount of from about 0.0001 wt./wt. % to about 3.0 wt./wt. %, with respect to the total composition of the preparation, using either lactoferrin itself or the N-terminal lactoferrin variant wherein at least the N-terminal glycine group has been cleaved off or replaced.

In order to be able to treat wounds, the preparation must be incorporated in a wound care treatment product, which can be a product that can be applied locally or with the aid of a carrier such as tulle (fatty gauze), an impregnated polyurethane foam sheet, impregnated foam or any standard wound care product or wound-healing means.

EXAMPLES OF WOUND CARE TREATMENT PRODUCTS

Example

An aqueous gel with a viscosity of between 1 and about 12,000,000 cP at room temperature, together with an amount of recombinant human lactoferrin (rhLF or an N-terminal lactoferrin variant wherein at least the N-terminal glycine group has been cleaved off or replaced), that is sufficient to improve the healing of wounds, and a polymer chosen from the list as mentioned above and in a concentration and having an average molecular weight as mentioned above.

Example 2

An aqueous gel (gel on the basis of water) with a viscosity of between 1 and about 12,000,000 cP at room temperature, together with an amount of lactoferrin that is sufficient to improve the healing of wounds, in a pharmaceutically acceptable polymer chosen from the list as mentioned above and in a concentration and having an average molecular weight as mentioned above.

Example 3

A third example of a wound care treatment product is a pharmaceutically acceptable carrier, wherein the preparation comprises lactoferrin in an amount that is sufficient to obtain an improvement in the healing of wounds, together with ozonized honey.

Example 4

Ointment/gel/cream consisting of:
75.3% of ozonized honey
12% of PEG 3500
12% of propylene glycol
0.5% of vitamin C
0.05% of vitamin E
0.05% of glucose oxidase
0.1% of lactoperoxidase

Example 5

Ointment/gel/cream consisting of:
15% of sunflower-seed oil
25% of ozonized honey
25% of PEG 4000
34.35% of propylene glycol
0.5% of vitamin C
0.05% of vitamin E
0.05% of glucose oxidase
0.1% of lactoferrin

Example 6

Ointment/gel/cream consisting of:
10% of soya-bean oil
40% of ozonized honey
15% of PEG 4000
34.1% of propylene glycol
0.5% of vitamin C
0.25% of vitamin E
0.05% of glucose oxidase
0.05% of lactoperoxidase
0.05% of lactoferrin

Example 7

Ointment/gel/cream consisting of:
10% of avocado oil
40% of ozonized honey
15% of CMC (sodium carboxymethylcellulose)
34.1% of propylene glycol
0.5% of vitamin C
0.25% of vitamin E
0.05% of glucose oxidase
0.1% of lactoperoxidase concerning the examples 4 to 7, the ointment/gel/cream can be applied on a gauze net, polyester net, polypropylene net, hydrocellular foam (made of polyurethane or another material) or alginate. The ointment/gel/cream is applied in an amount of 4-10 grams per 100 $cm^2$.

Example 8

The following materials can be used as a carrier according to the invention:
  woven or non-woven cotton gauze (standard in wound care)
  knitted multifilament polyester net with a density of 130/$m^2$
  knitted monofilament polypropylene, with a diameter of 0.14-0.20 mm polyacetate carrier
foam with:
- thickness between 0.3 cm and 1.5 cm
- density between 70 and 300 kg/m$^3$
- cell structure of 170-500 micrometres (μm)
- water absorption capacity after exudation or leakage of 10-20 g water/gram of foam
- water absorption capacity after compression of 10-14 g water/gram of foam
- moisture evaporation/transmission capacity of 3500-4500 g/m$^2$/24 hours
- linear swelling in the length direction of 15-30%
- linear swelling in the height direction of 15-25%
- ER/RR dry % elongation value of 200-450%
- ER/RR dry % strength at break of 100-300 kPa
- tensile strength of 2.5-8 kPa
- air permeability of 35-90 litres/min/dm$^2$.

Such a standard wound care treatment product can be applied for at least 1 week, 6 weeks, 12 weeks, 36 weeks, etc., or for any period of time in between.

An unbaked biscuit prepared from food fibres and/or by-products of food fibres and honey according to the invention is made from ozonized food fibres and/or by-products of food fibres and comprises raw, unheated honey that has been ozonized by a method according to the invention as described above. These food fibres can therewith consist of cereal grains such as wheat or oats, and the by-products of these food fibres can for instance consist of wheat bran or wheat germ and/or oat bran or oat germ.

The ozonized food fibres and/or ozonized by-products of food fibres are prepared by the diagram shown in FIG. 1 but in two stages, i.e.
- a first stage wherein ozone gas is blown through the food fibres for 1 to 2 hours,
- and after a rest period of almost 12 hours, a second stage wherein ozone gas is blown through the food fibres for 5 to 8 hours.

The biscuit can herewith also comprise one or more auxiliary substances, such as glycerol and aromatic flavouring agents.

EXAMPLES OF UNBAKED BISCUITS

Example 1

Biscuit consisting of:
39% of ozonized honey
30% of ozonized wheat bran
30% of ozonized wheat germ
0.5% of glycerol
0.25% of vanilla concentrate
0.25% of apple concentrate Example 2

Biscuit consisting of:
33% of ozonized honey
33% of ozonized wheat bran
33% of ozonized wheat germ
0.5% of glycerol
0.25% of vanilla concentrate
0.25% of apple concentrate Example 3

Biscuit consisting of:
28% of ozonized honey
35% of ozonized wheat bran
36% of ozonized wheat germ
0.5% of glycerol
0.25% of vanilla concentrate
0.25% of apple concentrate

The invention claimed is:

1. A method for sterilizing raw, unheated honey, wherein a composition consisting of raw, unheated honey is sterilized by producing ozone in an ozone generator and passing the ozone through the raw honey and ozonizing the honey with the ozone from the ozone generator.

2. Method according to claim 1, wherein the ozonizing the raw honey produces a sterilized raw honey that comprises substantially no fungi and yeasts and less than 100 colony-forming units per gram of viable aerobic bacteria.

3. Method according to claim 2, wherein the ozonizing the raw honey comprises providing $O_2$ at 1.2 bar, supplying the $O_2$ to an ozone generator producing 120 g/hour (24 g/Nm$^3$) of ozone at a flow rate of 15 l/min and an ozone pressure of 1 bar.

4. Method according to claim 1, wherein the raw unheated honey is provided at an ambient temperature of 35° C. and is warmed to a temperature of at most 40° C. for liquifying the raw unheated honey sufficiently, and contacting the liquefied raw honey such that the ozone comes into optimal contact with the raw honey.

5. The method of claim 1, further comprising:
supplying water,
cooling the water,
flowing the cooled water into and through the ozone generator,
placing the raw unheated honey in tall, narrow containers,
partially submerging the containers in a tank,
flowing water from the ozone generator into and through the tank,
warming the containers with the water in the tank,
flowing the water out of the tank and into the cooler,
flowing ozone from the ozone generator into pipes extending into the containers and to bottoms of the containers,
releasing none from the pipes,
dividing the pipes into plural pipes in the containers,
releasing the ozone from the plural pipes into bottoms of the containers, and
passing ozone through the raw unheated honey in the containers, thereby sterilizing and ozonizing the raw unheated honey.

* * * * *